(12) United States Patent
Clarke et al.

(10) Patent No.: US 8,857,984 B2
(45) Date of Patent: Oct. 14, 2014

(54) APPARATUS AND METHOD FOR ASSESSMENT AND REHABILITATION AFTER ACQUIRED BRAIN INJURY

(75) Inventors: Gayle Clarke, Semaphore Park (AU); Allison Dorothy Hayes, Semaphore Park (AU); Gregory William Liddle, Semaphore Park (AU); Raymond John Liddle, Semaphore Park (AU); Donald Frederick Verlander, Semaphore Park (AU)

(73) Assignees: Raymond John Liddle, South Australia (AU); Gregory William Liddle, South Australia (AU)

( * ) Notice: Subject to any disclaimer, the term of this patent is extended or adjusted under 35 U.S.C. 154(b) by 1077 days.

(21) Appl. No.: 12/158,175

(22) PCT Filed: Dec. 20, 2006

(86) PCT No.: PCT/AU2006/001946
§ 371 (c)(1),
(2), (4) Date: Sep. 15, 2008

(87) PCT Pub. No.: WO2007/070953
PCT Pub. Date: Jun. 28, 2007

(65) Prior Publication Data
US 2009/0009714 A1    Jan. 8, 2009

(30) Foreign Application Priority Data
Dec. 20, 2005   (AU) ................................ 2005907129

(51) Int. Cl.
*A61B 3/00* (2006.01)
*A61B 3/024* (2006.01)
*A61B 5/16* (2006.01)

(52) U.S. Cl.
CPC ................. *A61B 3/024* (2013.01); *A61B 3/005* (2013.01); *A61B 3/0091* (2013.01); *A61B 5/161* (2013.01); *A61B 5/168* (2013.01)
USPC ........................................... 351/203; 351/237

(58) Field of Classification Search
USPC .................................................. 351/203, 237
See application file for complete search history.

(56) References Cited

U.S. PATENT DOCUMENTS

| | | | | |
|---|---|---|---|---|
| 4,135,502 A | * | 1/1979 | Peck | 351/203 |
| 4,202,601 A | * | 5/1980 | Burbo et al. | 359/409 |
| 4,679,920 A | | 7/1987 | Takashi et al. | |
| 4,726,272 A | | 2/1988 | O'Brien et al. | |
| 4,854,694 A | * | 8/1989 | Hirano et al. | 351/224 |

(Continued)

FOREIGN PATENT DOCUMENTS

| | | |
|---|---|---|
| CA | 2301926 | 7/2000 |
| CA | 2388199 | 11/2003 |

(Continued)

*Primary Examiner* — James Greece
(74) *Attorney, Agent, or Firm* — Greenblum & Bernstein, P.L.C.

(57) ABSTRACT

The present invention relates to an apparatus and method for the assessment and rehabilitation of vision impairment. In particular, the invention is concerned with an apparatus displaying visual stimuli and the method of using this device for the purpose of assessment and rehabilitation of individuals with acquired brain injury and visual impairment resulting therefrom. The apparatus comprises a display means with a plurality of visual stimuli switched on and off in predetermined sequences. The sequences are adapted to be used to assess and rehabilitate a person's visual impairment.

16 Claims, 2 Drawing Sheets

(56) References Cited

U.S. PATENT DOCUMENTS

| | | | |
|---|---|---|---|
| 4,971,434 A | 11/1990 | Ball | |
| 5,035,500 A | 7/1991 | Rorabaugh et al. | |
| 5,094,521 A * | 3/1992 | Jolson et al. | 351/210 |
| 5,241,332 A | 8/1993 | Farrell | |
| 5,302,981 A * | 4/1994 | Wirtz | 351/246 |
| 5,534,953 A * | 7/1996 | Schmielau | 351/203 |
| 5,805,270 A | 9/1998 | Marshall | |
| 5,852,489 A | 12/1998 | Chen | |
| 5,900,923 A | 5/1999 | Prendergast et al. | |
| 6,206,702 B1 | 3/2001 | Hayden et al. | |
| 6,315,414 B1 | 11/2001 | Maddess et al. | |
| 6,364,845 B1 | 4/2002 | Duffy et al. | |
| 6,406,437 B1 | 6/2002 | Zur et al. | |
| 6,431,708 B2 | 8/2002 | Krebs | |
| 6,464,356 B1 | 10/2002 | Sabel et al. | |
| 2001/0048503 A1 | 12/2001 | Krebs | |
| 2004/0015098 A1 | 1/2004 | Souvestre | |
| 2004/0212778 A1 * | 10/2004 | Velazquez | 351/158 |
| 2005/0065452 A1 * | 3/2005 | Thompson | 600/558 |
| 2007/0027406 A1 | 2/2007 | LaPlaca et al. | |

FOREIGN PATENT DOCUMENTS

| | | |
|---|---|---|
| DE | 19621960 | 4/1997 |
| GB | 2397391 | 7/2004 |
| RU | 2029496 | 2/1995 |
| RU | 2053703 | 2/1996 |
| WO | 90/01290 | 2/1990 |
| WO | 97/36273 | 10/1997 |
| WO | 99/49776 | 10/1999 |
| WO | 02/30291 | 4/2002 |
| WO | 2005/079332 | 9/2005 |

* cited by examiner

APPARATUS AND METHOD FOR ASSESSMENT AND REHABILITATION AFTER ACQUIRED BRAIN INJURY

FIELD OF THE INVENTION

The present invention relates to an apparatus and method for the assessment and rehabilitation of vision impairment. In particular, the invention is concerned with an apparatus displaying visual stimuli and the method of using this device for the purpose of assessment and rehabilitation of individuals with acquired brain injury and visual impairment resulting therefrom.

BACKGROUND OF THE INVENTION

Acquired brain injury refers to any type of brain injury that occurs after birth. That is, brain injury resulting from an event such as stroke, trauma, infection, disease or prolonged lack of oxygen. Persons affected by an acquired brain injury will often suffer from impaired vision, whereby typically the visual field of the person is significantly reduced. It is not uncommon for the person affected to lose sight or suffer from severe deterioration in typically one half of their normal visual field, while still retaining normal sight in the unimpaired portion.

Traditionally, the testing and diagnosis of the limitations of a person's visual field, is conducted either in a clinical confrontational manner or via the use of a visual field analyser. These tests effectively map out the patient's remaining visual field or sphere of vision, mapping where objects are visible and distinguished. Clinical confrontational testing involves a clinician quickly determining the patient's extent of vision loss by requesting that the patient fix their gaze on a central point whilst moving an object through their field of vision. This test may be undertaken with the use of a pen, or alternative object, and enables the clinician to study the appearance and movement of the patient's eyes. Visual field analysers also require a patient to fix their gaze at a central point while various lights or other visual stimuli are displayed. The patient then notes which stimuli are visible within their field of vision. With enough visual stimuli the patient's effective visual field can be mapped out accurately for diagnosis and rehabilitation purposes. Once the remaining visual field is determined and mapped out, a suitable rehabilitation program focussing on utilising the remaining vision can be devised.

The problem with a traditional visual analyser is that it has limited use for rehabilitation. Clinical confrontational testing is also limited in its rehabilitation capability and is used to monitor progress or recession not to administer therapeutic programs. Both these predominantly testing devices and methods offer little use in assisting the patient to utilise more effectively their remaining sight. This is as the patient's head is fixed in position and their gaze is fixed at a central point. By instructing the patient to move their head and eyes in order to view the stimuli, the patient can be taught to use their residual visual field more effectively.

Traditional methods of testing vision impairment and subsequent rehabilitation techniques are specific to the purpose of either analysing or rehabilitating the patient. In order to assess and map the patient's remaining field of vision, traditional vision analysing equipment requires an operator to fire the sequence of visual stimuli of varying intensity and record whether the patient has seen the stimuli. This effectively precludes the clinician or operator from observing the patient's eye behaviour and head movement during testing. The observation of movement is important in determining the extent of the patient's vision loss, as the patient may compensate and attempt to view the stimuli with their remaining vision. Also the vision analyser can only be used to map out the patient's visual field and in certain circumstances rehabilitate the patient's deteriorated vision, where they are able to distinguish between different stimuli. Traditional vision analysers are single stimuli devices and assessors using devices cannot detect differences in the client's attention to visual stimuli. Other problems arising from the use of traditional vision analysers are that patients are required to concentrate and focus on a central point for a lengthy period of time, causing fatigue and inaccuracy of results. The level of concentration and complexity of instructions required to complete the task, may also lead to a person who is suffering from other impairments, such as cognitive or language deficits, producing an inaccurate result.

The human eye has a tendency to focus on or move towards any new visual stimuli, making traditional visual analysers inaccurate in determining a visual field map. This phenomenon also makes progress analysis difficult to accomplish, as conditions cannot easily be replicated. Also standardised or repetitive tests can be inaccurate, as the patient may grow accustomed to the visual stimuli and move his/her eye accordingly.

It is therefore an object of the present invention to overcome or at least ameliorate one or more of the aforementioned problems or to provide the public with a useful alternative.

SUMMARY OF THE INVENTION

Therefore in one form of the invention there is an apparatus including a display means including a plurality of visual stimuli whereby said plurality of visual stimuli are switchable between on and off conditions in predetermined sequences whereby said predetermined sequences are adapted to be used to assess and rehabilitate a person's visual impairment.

Preferably said visual impairment is resultant from an acquired brain injury.

Preferably said display means is a display board whereby said plurality of visual stimuli are arranged in a spaced apart configuration on the display board so that said visual stimuli cover the extent of said person's visual field when said person is located in the desired viewing position.

Preferably said display board is of rectangular configuration and includes twenty said visual stimuli arranged equally spaced in two rows of ten and a marker fixed in the centre of said display board.

Preferably said display board is mounted horizontally on a supporting means whereby said supporting means is vertically adjustable.

Preferably said plurality of visual stimuli are light emitting devices capable of being switched on and off.

Preferably said light emitting devices are coloured.

Preferably said apparatus is adapted to be used to teach clinicians to assess and rehabilitate said persons using said predetermined sequences.

In another form of the invention there is a method for visually assessing and rehabilitating a person comprising a series of tests using a plurality of visual stimuli switchable between on and off conditions in predetermined sequences.

In preference said predetermined sequences corresponds to a series of tests for visual assessment and a series of tests for visual rehabilitation whereby said series of tests are performed by a clinician on said person.

In preference said series of tests for assessment are performed sequentially and are used to ascertain the level of rehabilitation required.

In preference said tests for assessment include:

a test to establish said person's capacity to understand instructions and respond to said visual stimuli, and to determine visual scanning behaviour;

a test to establish said person's presence of a visual field loss and ability to fixate on a central target;

a test to establish said person's ability to detect multiple visual stimuli and identify perceived changes in intensity of the visual stimuli;

a test to establish said person's degree of head and eye turn required to fixate on the perimeter of said person's affected visual field;

a test to establish said person's ability to attend to multiple visual stimuli;

a test to establish said person's ability to utilise a systematic searching or scanning pattern to detect said visual stimuli and observe said person's speed of scanning;

a test to establish whether said person can attend to said visual stimuli in the affected visual field whilst in the presence of changing visual stimuli in the unaffected visual field;

a test to reinforce said person's strategy of scanning from the perimeter of the affected visual field and the limitations of vision in the affected visual field.

In preference said tests for rehabilitation include:

a test to define said person's width of visual field on said display means and to allow a comparison with the visual field width assessment;

a test to reinforce the degree of head and eye turn necessary for said person to fixate on the perimeter of the affected visual field, to reduce the amount of prompting needed for said person to fixate on the perimeter and to establish a pattern of scanning from the perimeter of said affected field towards a mid-line of said display means;

a test to reinforce said person's ability to scan from the perimeter of the affected visual field, to attend to multiple visual stimuli and to increase said person's ability to anticipate the presence of visual information in the absence of visual cues;

a test to reinforce said person's scanning pattern from the perimeter of the affected visual field towards said mid-line, to reduce said person's amount of prompting needed to establish and maintain a systematic search pattern and to establish a speed of scanning allowing for consistent and accurate detection of visual stimuli;

a test to reinforce the scanning pattern from the perimeter of the affected visual field to said mid-line to reinforce said person's ability to maintain attention in the affected visual field whilst said visual stimuli are displayed in the unaffected visual field, and to increase the speed at which said person can detect changes in said visual stimuli;

a test to reinforce said person's ability to scan from the perimeter of the affected visual field and to identify any difficulties regarding said person's spatial reasoning and spatial memory.

In preference said series of tests for rehabilitation provides the person with strategies to scan the entire visual range including the affected visual area so as the person may partake in general daily living activities safely.

Preferably said method of assessing and rehabilitating is further adapted to teach said clinicians to conduct said series of tests for assessment and said series of tests for rehabilitation utilising said apparatus.

In preference said teaching of clinicians further includes:

training to use the apparatus to display said sequences of light emitting devices;

training to conduct said series of tests for assessment and said series of tests for rehabilitation; and training to recognise said person's ability to complete said series of tests and whether further rehabilitation is required.

In preference said training to recognise said person's ability to complete said series of tests further includes:

an ability to understand and interpret the person with a visual impairment's eye and head movement; and an ability to ascertain the successfully completion of said series of tests for assessment and said series of tests for rehabilitation.

BRIEF DESCRIPTION OF THE DRAWINGS

The accompanying drawings, which are incorporated in and constitute a part of this specification, illustrate several implementations of the invention and, together with the description, serve to explain the advantages and principles of the invention. In the drawings.

DESCRIPTION OF THE PREFERRED EMBODIMENTS

The following detailed description of the invention refers to the accompanying drawings. Although the description includes exemplary embodiments, other embodiments are possible, and changes may be made to the embodiments described without departing from the spirit and scope of the invention.

Figure 1:
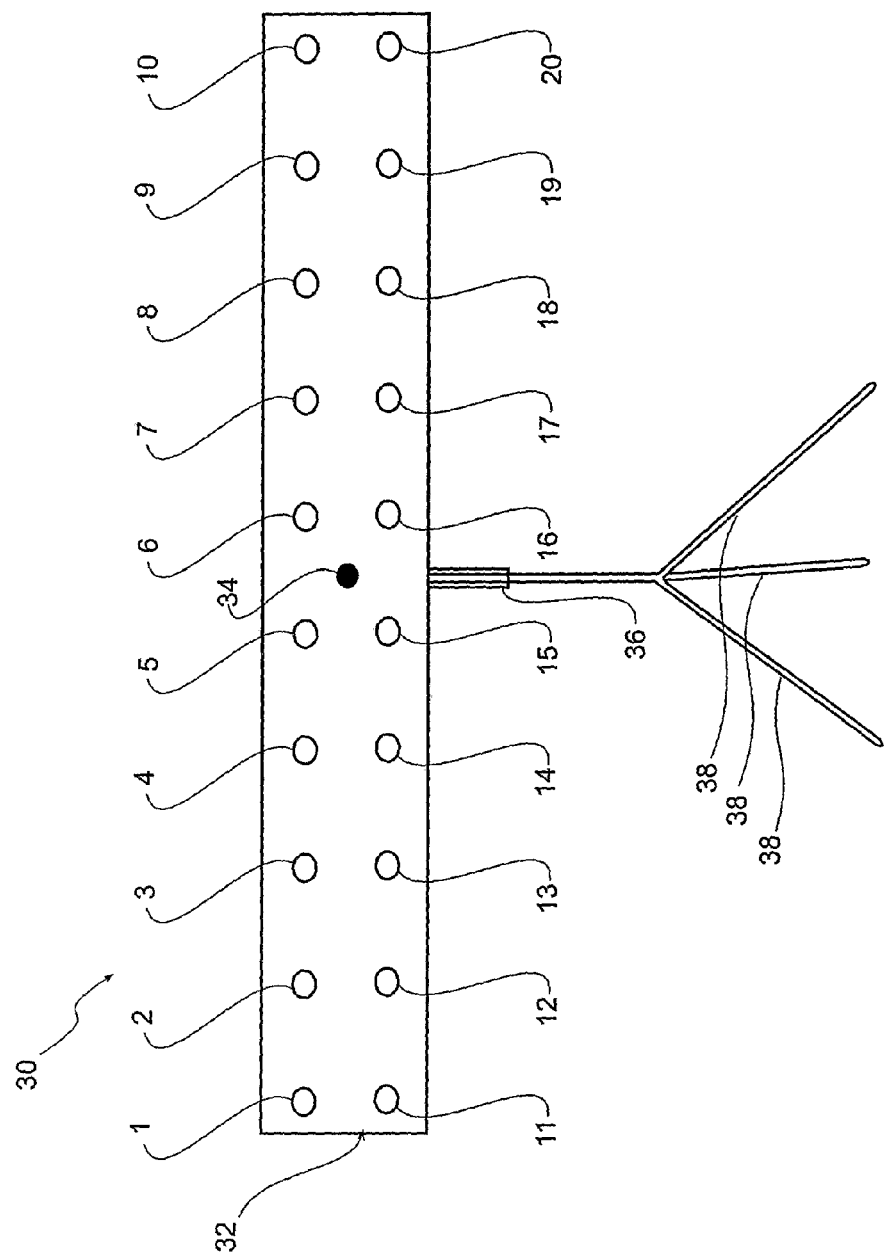
FIG. 1 illustrates an apparatus for the assessment and rehabilitation of individuals suffering vision impairment resulting from an acquired brain injury, in accordance with the invention.

FIG. 1 shows an apparatus for the assessment and rehabilitation of a client suffering vision impairment resulting from an acquired brain injury. The apparatus or scanning device 30 is the preferred embodiment of the present invention and consists of an array of visual stimuli arranged on a rectangular display board or panel 32 to assess and rehabilitate the client's visual range.

The client, requiring assessment and rehabilitation for impaired vision following an acquired brain injury, is seated in front of the scanning device 30 and approximately 300 mm away from the visual stimuli display board 32. The client is positioned so that his/her eye level is aligned with the central dot 34 in such a manner that a person with a full visual range would see all visual stimuli presented on the scanning device 30. Due to the varying physical conditions of the clients and their levels of mobility, the scanning device 30 has the ability to be moved and set up in the optimum assessing position. The display board 32 has the ability to have its viewing height adjusted 36, and the device's tripod base 38 can be manoeuvred so as to fit between the footplates of a wheelchair.

The display board 32 contains twenty visual stimuli; 1, 2, 3, 4, 5, 6, 7, 8, 9, 10, 11, 12, 13, 14, 15, 16, 17, 18, 19 and 20. These stimuli are preferably light emitting devices and will be referred to as lights herein. Also, the lights are preferably coloured red, blue, green, yellow and white. The lights are arranged equally spaced, about a central marking or dot 34, in two rows of ten. The central dot is used for the purpose of aligning the client's vision and is located in the centre of the display board 32. The clinician or therapist conducting the assessment and rehabilitation must take steps to correctly align the client's viewing position, avoid distractions or confusing backgrounds and eliminate glare shining on the display board 32. Once the client is comfortable, the therapist can conduct the test from a position opposite the site of the client's lesion. This enables the therapist to observe the client's behaviour whilst undertaking the tests in order to assess the client's effective use of their remaining visual field.

The scanning device 30 is also used an awareness tool for the client. The therapist must outline to the client the results of the assessment and the extent of the visual field loss. Once clients are aware of their own visual limitations, rehabilitation in maximising residual vision can take place to instruct the client to compensate for their loss. Assessment of the client's visual field using the scanning device 30 has two main aspects; to outline the client's actual visual field and to observe the extent of head turn required for the client to see all the visual stimuli. The scanning device 30 possesses the advantage over prior art vision analysers by allowing the ability to display multiple visual stimuli simultaneously.

The method for using the apparatus, for the assessment and rehabilitation of the client, involves the clinician or therapist overseeing and performing a series of tests. These tests are performed sequentially and the patterns displayed by the visual stimuli, for the client to view and acknowledge, progressively increase in difficulty. For the tests to be conducted satisfactorily, the therapist must undertake training to understand, diagnose and draw suitable conclusions from the client's behaviour. Training involves instructions to guide and assist the client though the tests and to recognise the client's ability to view the stimuli and conduct the tests accordingly. The rehabilitation process is complete when the client has undertaken and successfully completed all the relevant tests and demonstrated a consistent head movement to compensate for any loss in visual field. Also the client can demonstrate a scanning speed allowing for the accurate detection of all stimuli and a scanning frequency corresponding to the ability to negotiate daily activities. Training in the administration of the tests, using the scanning device 30, is given in the following areas: determining the amount and nature of cuing required, monitoring a client's fatigue levels, demonstrating the functional implementations of good scanning strategies, and observing a client's speed of visual processing in relation to the speed required to perform daily activities.

This wide scope of training is required due to the versatility of the scanning device 30 and its use in a variety of configurations. It can be brought to the client and assembled on site, the tests utilising the device do not require complex instructions, nor does the client have to possess any verbal communication skills. Hence, it can be used at any time following an acquired brain injury. The tests, utilising the scanning device 30 and detailed herein are used for the purpose of assessment and rehabilitation.

For the purpose of assessment, the first test to be undertaken on the scanning device 30 is a test for Spontaneous Scanning. The purpose of this test is for the therapist to gain an understanding of the location and extent of the client's visual field deficit and a measure of the client's ability to understand instructions. The light sequences are related to assessing whether the client possesses a suspected left or right hand side visual deficit. Two different light sequences are used, as clients can possess left or right hand hemianopia, where impairment exists in one half of the visual field in one or both eyes. For both the sequences visual stimuli, in the form of lights on the display board 32, are illuminated.

A trial light sequence is used for the purpose of determining the client's ability to understand instructions. The light sequence order for a client with left hemianopia is: 7, 6, 14, 20, 3, 9. This sequence corresponds to an initial light being displayed in the unaffected visual field and the therapist noting the client's ability to acknowledge the stimuli. This process is repeated until the therapist has determined the fastest speed possible for the client to detect and respond to the stimuli. This speed is used for subsequent tests of Spontaneous Scanning and Visual Field Assessment. The test sequence light order for the purpose of assessing whether or not the client can effectively: scan to the visually impaired side, scan to the perimeter of the affected visual field, or scan effectively across the full visual field, is as follows: 2, 19, 13, 16, 4, 1, 10, 15, 12, 18, 5, 17, 8, 11, 7, 6 14, 20, 3, 9. For a client with right hemianopia, the trial sequence is: 14, 15, 7, 1, 18, 12 and the test sequence is: 19, 2, 8, 5, 17, 20, 11, 6, 9, 3, 16, 4, 13, 10, 14, 15, 7, 1, 18, 12.

Once the therapist is satisfied that the client is comfortable with the assessment and their scanning response is consistent, the next test can be applied. The second test is a Visual Field Assessment and it aims to establish the presence of a visual field loss. The client is asked to fix their gaze at the central dot 34 and maintain a fixed head position throughout this test for the purpose of establishing the perimeter of vision. The light sequence for a client with left hemianopia is: 7, 6, 14, 20, 3, 9, 2, 19, 13, 16, 4, 1, 10, 15, 19, 12, 18, 5, 17, 8, 11. For a client with right hemianopia it is: 14, 15, 7, 1, 18, 12, 19, 2, 8, 5, 17, 20, 11, 6, 9, 3, 16, 4, 13, 10. These sequences can be used to determine the client's ability to maintain fixation on the central dot 34, whilst in the presence of additional visual stimuli. Also the speed at which the client observes the sequence of lights is noted. The therapist notes those lights that have not been detected in order to determine if there is an absolute visual field loss in the case where all lights in a particular field were missed. If inconsistencies occur in lights detected in a particular field the therapist will administer the test for relative field loss.

The test for Relative Field Loss involves the client fixating on the central dot 34, whilst pairs of same coloured lights are displayed on the display board 32. If the client can see the pair of lights and perceives them to be of the same intensity, brightness and colour then no relative visual field loss exists. If the client cannot detect multiple lights, can only detect lights in one quadrant or notes changes in light intensity in certain visual areas, then further analysis tools and assessment may be required. This further assessment is outside the scope of the scanning device 30. The corresponding light sequence is to illuminate; both green lights (4, 17) and if the client can identify both lights repeat with presentations of white (13, 3), red (6, 15), blue (5, 16) and green lights (12, 9).

The next test, Establishing a Perimeter, establishes the amount of head and eye turn required for the client to fixate on the perimeter of the affected visual field. It also allows for the therapist to establish the degree of cueing and prompting required for the client to fixate on the perimeter of the affected field. This test reinforces to the client the need to scan until all visual stimuli are observed and what degree of head turn is needed to effectively scan the entire visible field. The light sequence for a client with left hemianopia is: 1, 6, 1, 5, 2, 15, 1, 17, 1. For right hemianopia: 20, 15, 20, 16, 19, 6, 20, 4, 20. In both sequences the red light at the periphery of the affected visual field is displayed and the client is asked to scan, utilising both head and eye movement, until the light is seen. The degree of scanning required to view the periphery of the affected field is thus reinforced to the client, and further lights are displayed on the scanning device 30 in order to check for both accuracy and consistency in scanning.

If the therapist is satisfied the client can maintain consistent scanning, then the client moves onto the next assessment test, establishing whether or not the client can detect multiple simultaneous stimuli. In the Two/Three Light tests, the client is required to attend to multiple visual stimuli and maintain the ability to scan to the perimeter of the affected visual field in the presence of multiple visual stimuli. If the client is unable to do so, rehabilitation at this level should be undertaken. If the client can successfully perform this test, the client can then progress to the next assessment test. The method of testing for the following light sequences involves illuminating initially two lights, then three lights simultaneously and asking the client to name the colours. The two light test sequence for a client with left hemianopia is: (15, 16), (14, 16), (1, 2), (11, 13). For three lights: (14, 5, 17), (1, 3, 6), (12, 14, 8), (11, 3, 14). The two light test sequence for a client with right hemianopia is: (6, 5), (7, 5), (20, 18), (10, 8). For three lights: (7, 16, 4), (20, 18, 15), (9, 7, 13), (10, 18, 14). This test using the scanning device 30 allows for an assessor to determine whether the client, in the presence of multiple visual stimuli, misses the stimuli in the affected field whilst concentrating on the stimuli in the intact visual field.

The Lights Across The Board test allows for the therapist to determine whether the client is using a systematic searching or scanning pattern to detect the visual stimuli and whether that speed of scanning is suitable to be of functional use to the client in negotiating daily activities. If the client is unable to demonstrate a systematic approach to scanning, then the client should begin rehabilitation to address this issue. The light sequence for the assessment commences with four lights displayed simultaneously on the top row for left hand hemianopia in the left visual field, or the bottom row for right hand hemianopia in the right visual field. The client is then asked to indicate which lights are displayed. The test is repeated with five lights displayed on alternate rows and then with six or more lights displayed on both the top and bottom rows. For a client with left hemianopia is the light sequence is: (1, 3, 6, 8), (12, 14, 17, 19), (1, 12, 14, 5, 8, 19), (1, 2, 3, 12, 14, 15, 6, 8, 19, 20), (1, 2, 12, 4, 5, 16, 15, 8, 18, 19, 10). The light sequence for a client with right hemianopia is: (20, 18, 15, 13), (9, 7, 4, 2), (20, 9, 7, 16, 13, 2), (20, 19, 18, 9, 7, 6, 15, 13, 2, 1), (20, 19, 9, 17, 16, 5, 6, 13, 3, 2, 1). Following the completion of this assessment test, the therapist should be able to determine whether the client can use a systematic approach to view stimuli, can scan at a speed required to view all the stimuli, and has the ability to change tasks from counting to naming the stimuli. If the client has difficulty naming, pointing or counting the stimuli, the client may possess cognitive difficulties or dyspraxia and further assessment may be required.

The next test, named Two/Three Light Order, relates to establishing whether the client can attend to visual stimuli in their affected visual field whilst in the presence of changing stimuli in the unaffected field. The therapist should then note the speed at which the client detects the stimuli in the impaired visual field. In this test, two or three lights are displayed at one time and the client must distinguish the order in which lights are turned off. If the client is successful in maintaining attention on the lights in the impaired field of vision at various speeds, then the client has demonstrated the ability to process visual stimuli in a dynamic environment and can progress to the next assessment test. If not, then the client should undergo rehabilitation to achieve this. The light sequence for the two lights test for a client with left hemianopia is: (15, 16) 15 out first, (15, 16) 16 out first, (6, 7) 6 out first. For a three lights test: lights (14, 6, 17) are lit, with the lights turning off in the order; 6, 14, 17. Lights (14, 6, 17) are lit again and are turned off in the order; 14, 17, 6. Lights (14, 6, 17) are lit again and are turned off in the order; 17, 14, 6. The light sequence for the two light test for a client with right hemianopia is: (6, 5) 6 out first, (6, 5) 5 out first, (15, 14) 15 out first. For a three light test: lights (7, 15, 4) are lit, with the lights turning off in the order; 15, 7, 4. Lights (7, 15, 4) are lit again and are turned off in the order; 7, 4, 15. Lights (7, 15, 4) are lit again and are turned off in the order; 4, 7, 15.

In the Left/Right Comparison test, the therapist aims to reinforce the strategy of scanning from the periphery of the client's impaired or affected field of vision and determine whether the client is having any difficulties in spatial reasoning and memory. Also the test demonstrates to the client, and any potential carers, the existence of the affected visual field and that the client may miss one side of an item placed anywhere in their environment.

In this test the client is asked to compare the lights on the right, with the left and describe whether the pattern is a repetition. If the pattern is not symmetrical the client can also be asked how they would alter the lights displayed so that the left and right sides are symmetrical. The light sequence for a client with left hemianopia begins with: left hand side displaying lights (12, 3, 14) and right hand side (17, 8, 19),—left and right sides are symmetrical repeating pattern. Left side lights (1, 2, 3, 14) compared with right (7, 8, 19)—left and right sides are a different pattern. Left side lights (11, 2, 13, 4) compared with right (7, 8, 9)—left and right sides are a different pattern. The test also involves lights on both sides of the display board 32 being lit with the left hand side displaying (1, 12, 3, 4) and right (7, 18, 19). The client is then asked what lights need to be changed in order to change the pattern on the right hand side to match that of the left. The light sequence for a client with right hemianopia begins with: left hand side (12, 3, 14) and right hand side (17, 8, 19)—left and right sides are a symmetrical repeating pattern. Left side lights (2, 13, 14) compared with right (7, 18, 19, 20)—left and right sides are a different pattern. Left side lights (2, 13, 4) compared with right (7, 13, 9, 10)—left and right sides are a different pattern. The test also involves lights on both sides of the display board 32 being lit with the left hand side displaying (12, 3, 4) and right (17, 18, 9, 20). The client is then asked what lights need to be changed in order to change the pattern on the left hand side to match the right. If the client successfully completes this test then further assessment using the scanning device is not required and the client may move on to mobility assessment or other assessment methods. At this point, the client should understand the results of the assessment and the effective use of scanning strategies to compensate for any visual field deficits. If the client cannot comprehend this then rehabilitation reinforcing the limitations of their existing visual field needs to be undertaken.

Figure 2:
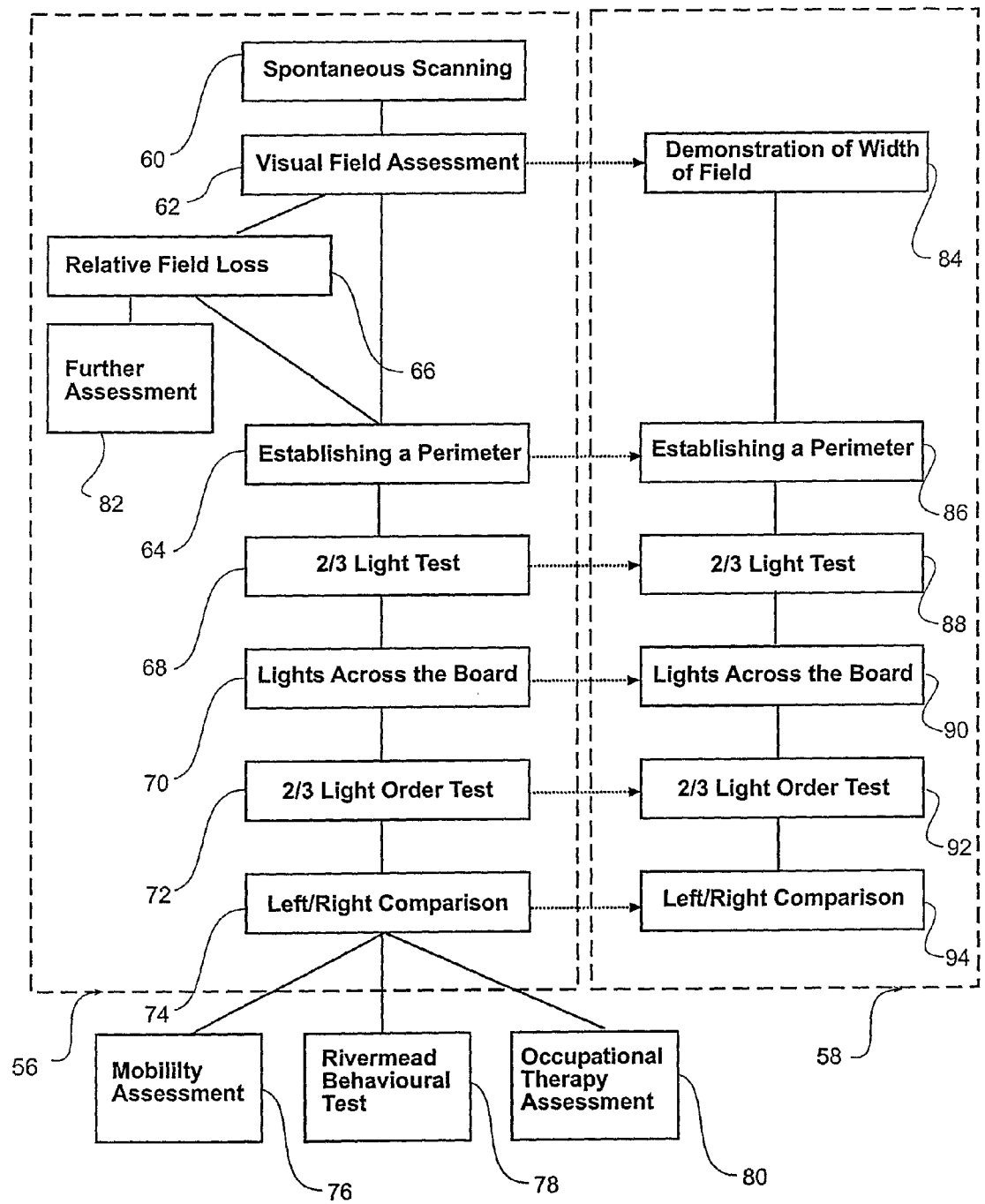
FIG. 2 illustrates a flow chart outlining the relationship between assessment and rehabilitation tests using the apparatus for assessment and rehabilitation shown in FIG. 1.

FIG. 2 outlines the relationship between the assessment 56 and rehabilitation 58 tests using the scanning device 30 and their sequence following successful completion. It can be seen in FIG. 2, that the use of the scanning device with respect to the assessment and rehabilitation of a client following an acquired brain injury, begins with the assessment tests 56 for the client.

The test for Spontaneous Scanning 60 is first conducted, followed by the client's Visual Field Assessment 62. If no absolute visual field loss is detected a test for Relative Field Loss is conducted 66. If the client is unable to describe the difference between the identical coloured stimuli or lights, then further assessment 82, outside the scope of the scanning device 30 is required. Otherwise the client's assessment proceeds with Establishing the Perimeter 64 of the client's affected visual field. The subsequent tests are; a Two/Three Light exercise 68 to determine the client's ability to attend to multiple stimuli, a test for evidence of a systematic search pattern (Lights Across the Board) 70, a test to establish whether the client can attend to stimuli in the affected field (Two/Three Light Order) 72, and a test to reinforce the scanning strategy (Left Right Comparison) 74. If during any of these exercises, the client is not successful in completing the assessment, rehabilitation exercises using the same techniques as the assessment tests can be applied where needed. Shown in FIG. 2, is the relationship between assessment and the corresponding rehabilitation tests, 84, 86, 88, 90, 92 and 94.

The rehabilitation test for demonstrating the width of the client's visual field 84, utilising the scanning device 30, is used to illustrate to the client the increase in effective visual field when appropriate scanning patterns are utilised. The sequence of lights on the display board 32 for this rehabilitation test demonstrating the width of the visual field begins, for a client with left hemianopia, with the left most light 1, followed by the right most light 10. The lights between the two are then turned on progressively. For a client with a right hemianopia, the light sequence begins with the right most light 20, followed by the left most light 11, and the lights between the two are progressively turned on.

The light sequences for the rehabilitation tests 86, 88, 90, 92, 94, correspond to the assessment test light sequences described above, utilising repetition of similar patterns to reinforce the ideas conveyed. For this reason the full light sequences of the repetitive rehabilitation tests will not be detailed. The sequences for both assessment and rehabilitation are stored digitally and retrieved when a therapist uses that particular element of a software package. There also exists the ability for the therapist to illuminate the visual stimuli displayed on the scanning device 30 manually.

The procedure for the rehabilitation test, Establishing a Perimeter 86, is the same as the corresponding assessment test and the first rehabilitation light sequence is the assessment sequence. The method of rehabilitation involves: illuminating the red light at the periphery of the affected visual field and guiding the client to the perimeter through prompting and hence reinforcing to the client the amount of head turn required to scan to the end of the display board 32. Once the client is focused on the periphery light, turn the light off and illuminate a second light near the middle of the display board 32. Continue alternating between single lights, on the perimeter of the affected field and a light near the central dot 34, in order to reinforce to the client the ability to scan to the perimeter of the affected visual range consistently.

The procedure for the rehabilitation tests, Two/Three Light Exercise 88 and the Two/Three Light Order 92, are the same as the corresponding assessment tests and aim to reinforce to the client that a consistent scanning pattern from the perimeter of the affected field needs to be implemented. Through repetition of similar light sequences, the client is able to attend to multiple stimuli and increase the attention given to the affected visual field. The Lights Across the Board 90 rehabilitation test further reinforces that the client must perform a scanning pattern from the perimeter of the affected field towards the midline. Through the repetition of light sequences the client is able to establish a functional speed of scanning corresponding to the ability to negotiate his/her way through tasks of daily living. The last rehabilitation test, Left/Right Comparison 94, through repetition of similar light sequences, reinforces to the client the strategies of scanning from the perimeter of the affected visual field. This test introduces additions and variations in lights on the affected side when compared to the pattern of lights on the unaffected side a light in order to reiterate the importance of thorough scanning to reduce the probability of error. Other difficulties such as spatial reasoning and memory are also identified during this process and further assessment may be required.

After the successful completion of the assessment and rehabilitation of the client using the scanning device 30, the client should be able to effectively view the normal visual range by consistently scanning the length of the visual range using the remaining portion of their vision whilst moving their head and eyes. The speed of scanning should be sufficient to allow the client to perform daily living activities without assistance. In order to assist the client with these daily living activities, mobility exercises reinforcing the scanning techniques developed using the scanning device 30 are performed with the assistance of a clinician or therapist. These are real life scenario based exercises aimed at reinforcing to the client the practical application of the scanning techniques learnt.

Further advantages and improvements may very well be made to the present invention without deviating from its scope. Although the invention has been shown and described in what is conceived to be the most practical and preferred embodiment, it is recognized that departures may be made therefrom within the scope and spirit of the invention, which is not to be limited to the details disclosed herein but is to be accorded the full scope of the claims so as to embrace any and all equivalent devices and apparatus.

In any claims that follow and in the summary of the invention, except where the context requires otherwise due to express language or necessary implication, the word "comprising" is used in the sense of "including", i.e. the features specified may be associated with further features in various embodiments of the invention.

The invention claimed is:

1. An apparatus for assessing and rehabilitating a person's visual impairment, the person's visual impairment defined by a visual field deficit as compared to an unaffected visual field where there is no visual impairment including a display, the display including a plurality of visual stimuli wherein said plurality of visual stimuli are arranged in a spaced apart configuration so as to substantially cover what would be the expected unaffected visual field of the person as defined with reference to a respective viewing position located in front of and spaced from the display, wherein said plurality of visual stimuli are switchable between on and off conditions in predetermined sequences to cause compensatory scanning movement of the head and eyes of the person viewing the display in order to assess and rehabilitate the person's visual impairment.

2. An apparatus as in claim 1 wherein said visual impairment is resultant from an acquired brain injury.

3. An apparatus as in claim 1 wherein said display is a display board.

4. An apparatus as in claim 3, wherein said display board is of rectangular configuration and said plurality of visual stimuli are arranged equally spaced in two rows.

5. An apparatus as in claim 3, wherein said display board is mounted horizontally on a support and wherein said support is vertically adjustable.

6. An apparatus as in claim 1 wherein said plurality of visual stimuli are light emitting devices capable of being switched on and off.

7. An apparatus as in claim 1 wherein said plurality of visual stimuli are coloured.

8. An apparatus as in claim 1 wherein said apparatus is adapted to be used to teach clinicians to assess and rehabilitate said persons using said predetermined sequences.

9. A method of assessing and rehabilitating a person's visual impairment, the person's visual impairment defined by a visual field deficit as compared to an unaffected visual field where there is no visual impairment, the method comprising:
   assessing the person's visual impairment using an apparatus including a display, the display including a plurality of visual stimuli such that said plurality of visual stimuli are switchable between on and off conditions in a first set of predetermined sequences to cause compensatory scanning movement of the head and eyes of the person viewing the display; and rehabilitating the person's visual impairment by switching the plurality of visual stimuli in a second set of predetermined sequences to develop head and eye scanning strategies to compensate for the visual field deficit.

10. An apparatus as in claim 1 wherein multiple visual stimuli of the plurality of visual stimuli are displayable simultaneously in the predetermined sequences.

11. An apparatus as in claim 3, wherein said display board includes a marker fixed in the centre of said display board for alignment of the eye level of the person.

12. A method of assessing and rehabilitating a person's visual impairment as in claim 9, wherein the head and eye scanning strategies include developing consistent head movement to compensate for the visual field deficit caused by the person's visual impairment.

13. A method of assessing and rehabilitating a person's visual impairment as in claim 9, wherein the head and eye scanning strategies include developing a scanning speed appropriate for the accurate detection of stimuli.

14. A method of assessing and rehabilitating a person's visual impairment as in claim 8, wherein the head and eye scanning strategies include developing a scanning frequency corresponding to the ability for the person to negotiate daily activities.

15. A method as in claim 9, wherein:
the display is a display board; and
the plurality of visual stimuli are arranged in a spaced apart configuration on the display board so that the plurality of visual stimuli substantially covers what would be the expected unaffected visual field of the person as defined with reference to a respective viewing position located in front of and spaced apart from the display.

16. A method as in claim 9, wherein the first set of predetermined sequences and the second set of predetermined sequences are substantially the same.

* * * * *